(12) United States Patent
Formica et al.

(10) Patent No.: US 6,228,658 B1
(45) Date of Patent: May 8, 2001

(54) METHOD OF USING A TEST STRIP FOR THE IMMUNOCHEMICAL DETECTION OF SUBSTANCES

(75) Inventors: Philip-Michael Formica; Rainer Polzius; Andreas Manns, all of Lübeck (DE)

(73) Assignee: Drager Sicherheitstechnik GmbH (DE)

( * ) Notice: Subject to any disclaimer, the term of this patent is extended or adjusted under 35 U.S.C. 154(b) by 0 days.

(21) Appl. No.: 09/199,134

(22) Filed: Nov. 24, 1998

(30) Foreign Application Priority Data

Jul. 8, 1998 (DE) ............................................... 198 30 405

(51) Int. Cl.[7] ........................................................ G01N 33/48
(52) U.S. Cl. ........................... 436/169; 436/901; 436/164; 436/816; 422/58
(58) Field of Search ................................ 422/56, 58, 61; 436/815–816, 901, 164, 169

(56) References Cited

U.S. PATENT DOCUMENTS 4,806,312 * 2/1989 Greenquist ............................ 422/58
5,140,986     8/1992 Klinger .
5,573,921 * 11/1996 Behnke et al. ........................ 422/56
5,602,040 *  2/1997 May et al. ............................. 422/60

FOREIGN PATENT DOCUMENTS

| 42 29 591 | 3/1994 | (DE) . |
| 44 39 429 C2 | 2/1996 | (DE) . |
| 196 45 569 | 3/1998 | (DE) . |
| 0 407 904 | 1/1991 | (EP) . |
| WO 97/19353 | 5/1997 | (WO) . |

* cited by examiner

*Primary Examiner*—Lyle A. Alexander
(74) *Attorney, Agent, or Firm*—McGlew and Tuttle, P.C

(57) ABSTRACT

A test strip for the immunochemical detection of substances after sampling from surfaces, with a conjugate zone (2) located between an eluent application zone (1) at one end of the test strip and a reaction zone (3) at the opposite end, the zones being in liquid connection with one another. A section of the test strip in the area including the eluent application zone and the reaction zone is used to wipe off the surface and as a sampling zone (4). The eluent application zone may be used as a sampling zone. The test strip is connected to a preferably flexurally rigid test strip holder (6), which does not cover the sampling zone (4).

8 Claims, 5 Drawing Sheets

METHOD OF USING A TEST STRIP FOR THE IMMUNOCHEMICAL DETECTION OF SUBSTANCES

FIELD OF THE INVENTION

The present invention pertains to a test strip for the immunochemical detection of substances after sampling from surfaces by wiping off.

BACKGROUND OF THE INVENTION

A process for detecting the contamination of a surface with an analyte by wiping off the analyte from the surface with a wiping surface separate from a test strip, contacting the wiping surface and the test strip and subsequently applying an eluent with a subsequent immunological binding reaction has become known from DE 44 39 429 C2. One drawback of this prior-art process and of the corresponding arrangement is that a separate wiping surface must be present for sampling, on the one hand, and, on the other hand, that a special housing for receiving the test strip and the wiping surface is provided for contacting the wiping surface and the test strip. In addition, the wiping surface must be contacted with the test strip with a minimum pressure, but without preventing or hindering the capillary flow of liquid in the test strip.

SUMMARY AND OBJECTS OF THE INVENTION

Thus, the primary object of the present invention is to provide a test strip, which has a simple design and is suitable for sampling from surfaces by wiping off, without having an additional wiping surface separate from the test strip.

According to the invention, a test strip for the immunochemical detection of substances after sampling from surfaces by wiping off is provided including:

a) A conjugate zone located between a eluent application zone at one end of the test strip and a reaction zone at the opposite end, the zones being in liquid contact with one another, and b) a section of the test strip in the area between and including the said eluent application zone and the said reaction zone is used to wipe off the surface and as a sampling zone.

The eluent application zone may be used as the sampling zone. The sampling zone may be arranged between the said conjugate zone and the reaction zone. The test strip may be laminated onto a carrier layer. The test strip may be connected to a preferably flexurally rigid test strip holder which does not cover the sampling zone.

The invention also provides a process for detecting substances by means of a test strip with the features a) and b) mentioned above. The process includes using the test strip with the following steps:

a) The surface to be tested for the substance to be detected is wiped off with a section of the test strip, which is located in the area including the eluent application zone and the reaction zone;

b) elution liquid is applied to the eluent application zone, so that elution liquid and the substance to be detected migrate in the direction of the reaction zone, and c) the presence of the substance to be detected in the reaction zone is measured based on an immunochemical detection reaction.

The test strip may be used in this way for detecting drugs. The test strip can be used for detecting low-molecular-weight harmful substances. Another advantageous use of the test strip is for detecting proteins and/or allergens. The test strip may also be used for detecting substances in body fluids of living beings.

One essential advantage of the present invention arises from the fact that no separate wiping surface needs to be provided for sampling, on the one hand, and that, on the other hand, no contacting needs to take place with the test strip, so that a corresponding housing for receiving and contacting the wiping surface and the test strip is eliminated.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
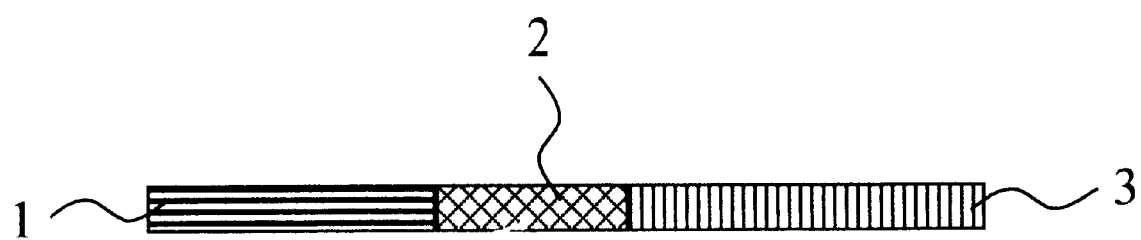
FIG. 1 is a view showing the general design of a test strip for the immunochemical detection of substances.

Referring to the drawings in particular, the capillary active chromatographic test strip may be of a one-piece or multiple-piece design and it comprises, in the general embodiment (see FIG. 1), an eluent application zone 1, a conjugate zone 2, and a reaction zone 3, which are physically connected to each other to be in liquid contact with one another as shown in the drawings. After applying an eluent to the eluent application zone 1, marked specific binding partners, which are deposited in the conjugate zone 2, are resolubilized and enter the reaction zone 3 by capillary action. The analyte, i.e., the substance to be detected, which is dissolved in the eluent, is detected in the reaction zone 3 by means of a specific binding reaction, preferably solid-phase reaction.

Figure 2:
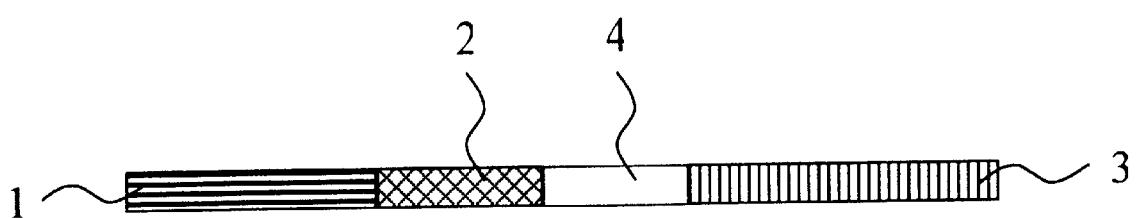
FIG. 2 is a schematic view showing the modified design of a test strip according to FIG. 1 with a sampling zone.

The sampling zone 4, which is used as a wiping surface, is an integral part of the test strip according to the present invention. The sampling zone 4 may be identical to the eluent application zone 1, the conjugate zone 2 or the reaction zone 3, or represent a partial area of the zones. In a preferred embodiment, the sampling zone 4 is arranged as an additional element between the conjugate zone 2 and the reaction zone 3 (see FIG. 2). The sampling zone 4 is in liquid contact with the conjugate zone 2 and the reaction zone 3 following it. After the application of the eluent to the eluent application zone 1, the analyte, which is enriched because of the wiping process in the sampling zone 4, is dissolved in the eluent due to the capillary liquid flow. The dissolved analyte can thus be detected in the reaction zone by means of the labeled binding partners.

Figure 3:
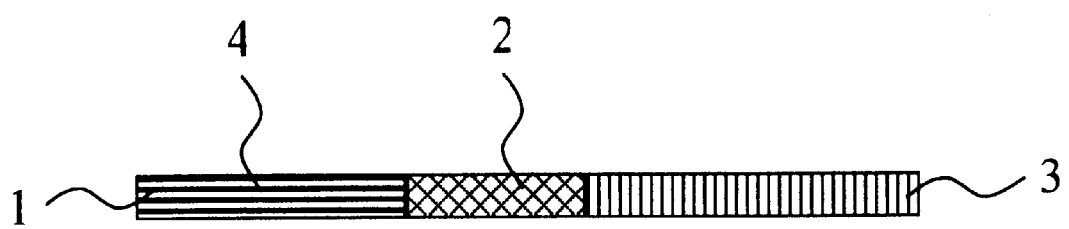
FIG. 3 is a schematic view showing modified design of a test strip according to FIG. 1, wherein the sampling zone and the eluent application zone are identical (in a common area)

In an especially preferred embodiment, the sampling zone 4 is identical to (in common with) the eluent application zone 1 (see FIG. 3). The analyte, enriched due to the wiping process in the sampling zone 4, is dissolved in the eluent after the application of the eluent to the eluent application zone 1 and is detected in the reaction zone 3 by means of labeled binding partners.

The sampling zone 4 may consist of any fibrous and/or porous material, which is able to absorb the analyte due to a wiping process and additionally has a capillary action, e.g., especially glass fibers, cellulose, plastics, or silica. Materials whose pore diameter is between 0.1 $\mu$m and 100 $\mu$m and which have a rate of linear water uptake of 1 mm/minute to 20 cm/minute are preferably used. Materials which are characterized by a pore diameter between 2 $\mu$m and 25 $\mu$m and a rate of linear water uptake of 1 cm/minute to 10 cm/minute are especially preferred. The layer thickness of the material may be between 100 $\mu$m and 0.5 cm. Polyester fibers and/or cellulose fibers have proved to be particularly suitable.

The area of the sampling zone 4 is typically between 0.1 and 5 cm$^2$. Especially preferred dimensions of the sampling zone 4 are between 0.5 and 4 cm (length) and 0.25 and 1 cm (width).

Water or buffered aqueous solutions with a pH value between 4 and 12, which may contain up to 50 vol. % of organic solvents, are preferably used as the eluent. Ionic and non-ionic detergents may also be contained in the eluent in an amount of 0.01 to 10 vol. %.

Figure 4:
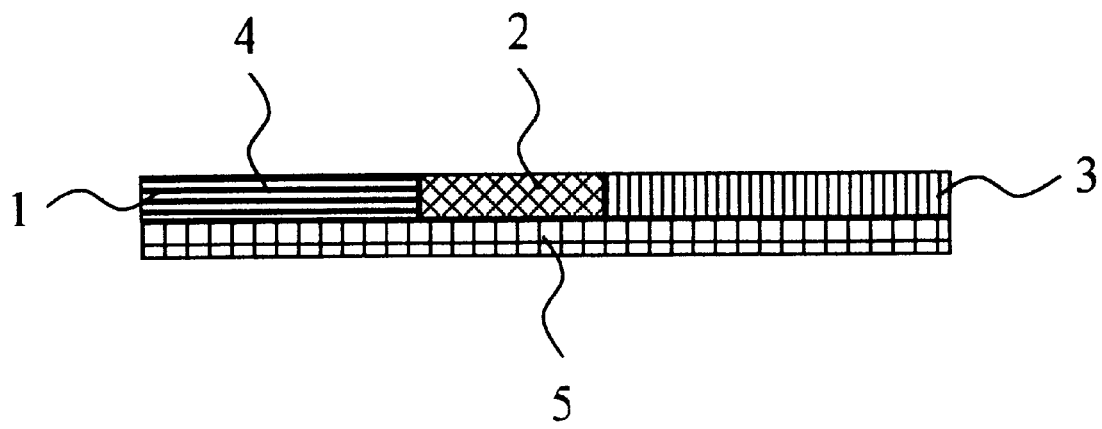
FIG. 4 is a schematic view showing the modified design of a test strip according to FIG. 3 with a laminated carrier layer.

To facilitate the wiping process for the user and to prevent the test strip from being damaged during wiping, the test strip may be laminated onto a flexurally rigid, flat carrier layer 5 (see FIG. 4) in another embodiment This causes the test strip to be able to be manually well guided during wiping without bending or breaking off.

Figure 5:
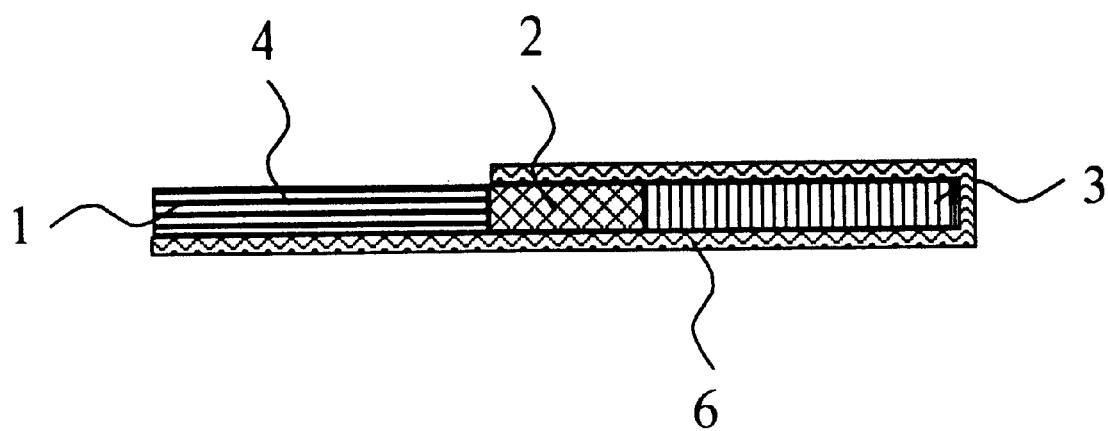
FIG. 5 is a schematic view showing the modified design of a test strip according to FIG. 3 with a connected, flexurally rigid test strip holder.

A flexurally rigid test strip holder 6, which receives the test strip such that the sampling zone 4 is exposed from the test strip holder 6 (see FIG. 5), is especially preferred. This offers the advantage that only the sampling zone 4 comes into contact with the surface to be tested during the wiping process and the test strip is protected from mechanical damage. After sampling, the test strip may be removed from the test strip holder 6 for the analysis. Especially preferable is an embodiment in which the test strip holder 6 is made of a transparent material in the reaction zone 3 and has an opening, so that the detection reaction can be visually detected. This offers the advantage that the test strip may remain in the test strip holder 6 for the analysis.

Synthetic and biological receptors, such as membrane receptors, enzymes and antibodies, may be used in the test strip. Detection reactions based on the antibody-antigen interaction have been known to the person skilled in the art as immunochromatography or as immunoconcentration. A specific binding partner is immobilized in the reaction zone 3 here. The coupling with the solid phase may be performed adsorptively, ionically, covalently or by bridging the specific binding partner with, e.g., protein A, avidin or latex particles. Depending on the format of the immunochemical detection, the solid-phase reaction consists of the formation of the complex of immobilized binding partner, the substance to be detected, and the labeled binding partner (two-sided test) or the complex of immobilized binding partner and labeled binding partner (competitive test). Antibodies, which may be monoclonal or polyclonal, or their fragments may be used as binding partners. Besides the specific antibodies or their fragments, the substance to be detected or derivatives of the substance to be detected, which may be coupled with macromolecules, may be used as binding partners in the competitive test. Embodiments in which the labeled binding partner is bound by a trapping zone and the labeled binding partners breaking through are indicated are preferred in the competitive test. This principle has been known from breakthrough chromatography.

The labeled binding partners are deposited in the conjugate zone 2. The labeling substances suitable for use as signal-generating components are enzymes, fluorophores, radioactive isotopes or colored particles. The use of direct optical markers, such as metal colloids or colored latex particles, as well as fluorophores, is especially suitable for the process according to the present invention.

Exemplary Embodiment

The present invention will be described below as an example based on the detection of traces of drugs on surfaces. The immunochromatographic test strips used for this purpose are based on the competitive format and correspond to the design shown in FIG. 4. The materials needed to prepare the test strips as well as the drug-specific antibodies and drug-protein conjugates may be obtained commercially and are known to the person skilled in the art. A polyester mat with a length of 2 cm and a width of 0.5 cm was used as the sampling zone 4 (also acting as the eluent application zone 1 at the same time).

a) Preparation of the Model Surface

Ten $\mu$L of a solution of the drug substance in methanol was applied at different concentrations to a glass plate. The solvent was evaporated at room temperature, so that spots of about 2 cm$^2$ containing different amounts of drug were obtained.

b) Wiping Off and Detection of the Drugs

The contaminated surface was wiped off for 10 sec under a gentle pressure with the sampling zone 4 of the immunochromatographic test strip specific of the analyte in question.

The immunochromatographic reaction was subsequently induced by applying 150 $\mu$L of phosphate buffer (80 mM, pH 7.6) to the eluent application zone 1. The color reaction was evaluated visually after 5 minutes. The color intensity in the reaction zone 3 is indirectly proportional to the concentration of the drug. As is shown in the table below, it was possible to detect very small quantities of the drug substance with the detection process according to the present invention.

| Type and amount of drug (ng) | Color reaction (visual) |
|---|---|
| d-Amphetamine sulfate (amphetamine) | |
| 4,000 | − |
| 1,000 | − |
| 250 | − |
| 62.5 | − |
| 16 | + |
| 0 | ++ |
| Alprazolam (benzodiazepine) | |
| 1,000 | − |
| 250 | − |
| 62.5 | − |
| 16 | − |
| 0 | ++ |

-continued

| Type and amount of drug (ng) | Color reaction (visual) |
|---|---|
| Morphine-3β-glucuronide (morphine metabolite) | |
| 2,000 | − |
| 500 | − |
| 125 | − |
| 31 | − |
| 8 | + |
| 0 | ++ |
| Benzoylecgonine (cocaine metabolite) | |
| 960 | − |
| 240 | − |
| 80 | − |
| 20 | + |
| 0 | ++ |

Legend:
−: No color reaction (negative test)
+: Weak color reaction (weakly positive test)
++: Intense color reaction (positive test)

Thus, the present invention may be used to detect both drugs and toxic or allergenic substances, using specific immunochemical detection reactions each time. The sampling may be performed on surfaces of objects and on living beings alike, so that substances in body fluids/secretions may also be tested.

While specific embodiments of the invention have been shown and described in detail to illustrate the application of the principles of the invention, it will be understood that the invention may be embodied otherwise without departing from such principles.

What is claimed is:

1. A process for detecting substances by means of a test strip, the process comprising the steps of:

providing a test strip with an eluent application zone, a reaction zone, a conjugate zone located between said eluent application zone at one end of the test strip and said reaction zone at the opposite end of the test strip, the zones being in liquid contact with one another, said eluent application zone being integal with the test strip said conjugate zone including deposited, labeled, specific binding partners for an immunochemical detection reaction in said reaction zone, where said reaction can be directly detected visually;

using said eluent application zone as a sampling zone and wiping the surface to be tested for the substance to be detected with said eluent application zone;

applying elution liquid to said eluent application zone so that elution liquid and the substance to be detected migrate in the direction of said reaction zone; and visually detecting and measuring the presence of the substance in said reaction zone based on said immunochemical detection reaction.

2. The process in accordance with claim 1, wherein said detecting and measuring the presence of the substance detects drugs.

3. The process in accordance with claim 1, wherein said detecting and measuring the presence of the substance detects low-molecular-weight harmful substances.

4. The process in accordance with claim 1, wherein said detecting and measuring the presence of the substance detects proteins and/or allergens.

5. The process in accordance with claim 1, wherein said detecting and measuring the presence of the substance detects substances in body fluids of living beings.

6. The process in accordance with claim 1, wherein
said sample zone is physically connected to said conjugate zone.

7. The process in accordance with claim 1, wherein
said sample zone, said eluent application zone, said reaction zone and said conjugate zone are physically connected to each other.

8. The process in accordance with claim 1, wherein
said labeled, specific binding partners include one of metal colloids, colored latex particles and fluorophores as optical labeling substances.

* * * * *